United States Patent [19]

Huang et al.

[11] Patent Number: 4,882,354

[45] Date of Patent: Nov. 21, 1989

[54] N-HYDROXY-5-PHENYL-2-FURANCARBOXIMIDAMIDES USEFUL AS CARDIOTONIC AGENTS

[75] Inventors: Chau-Ting Huang; Stanford S. Pelosi, Jr.; Allan V. Bayless, all of Norwich, N.Y.

[73] Assignee: Norwich Eaton Pharmaceuticals, Inc., Norwich, N.Y.

[21] Appl. No.: 133,577

[22] Filed: Dec. 16, 1987

[51] Int. Cl.$^4$ .......................................... C07D 307/66
[52] U.S. Cl. .................................... 514/461; 549/491
[58] Field of Search ........................ 549/491; 514/461

[56] References Cited

U.S. PATENT DOCUMENTS

| | | | |
|---|---|---|---|
| 3,906,010 | 9/1975 | Pelosi, Jr. | 549/491 |
| 3,946,049 | 3/1976 | Pelosi, Jr. | 549/491 |
| 3,985,891 | 10/1976 | Kutter et al. | 424/263 |
| 4,004,012 | 1/1977 | Lesher et al. | 424/263 |
| 4,012,414 | 3/1977 | Pelosi, Jr. | 260/309 |
| 4,012,415 | 3/1977 | Pelosi, Jr. et al. | 260/309 |
| 4,012,416 | 3/1977 | Pelosi, Jr. | 260/309 |
| 4,021,444 | 5/1977 | Pelosi, Jr. | 260/309.6 |
| 4,022,798 | 5/1977 | Pelosi, Jr. | 260/309.6 |
| 4,032,575 | 6/1977 | Ikezaki et al. | 260/570.6 |
| 4,289,772 | 9/1981 | Campbell et al. | 424/250 |
| 4,297,360 | 10/1981 | Lesher et al. | 424/263 |
| 4,397,854 | 8/1983 | Sircar | 424/250 |
| 4,405,635 | 9/1983 | Schnettler et al. | 424/273 R |
| 4,705,782 | 11/1987 | Logan et al. | 514/150 |

FOREIGN PATENT DOCUMENTS

| | | | |
|---|---|---|---|
| 158380 | 10/1985 | European Pat. Off. | 549/49 |
| 199393 | 10/1986 | European Pat. Off. | 549/49 |

*Primary Examiner*—Mary C. Lee
*Assistant Examiner*—Zinna Northington-Davis
*Attorney, Agent, or Firm*—Milton B. Graff, IV; David L. Suter; Jack D. Schaeffer

[57] ABSTRACT

The present invention involves certain N-hydroxy-5-phenyl-2-furancarboximidamides, pharmaceutical compositions containing such compounds, and methods for increasing the contractile force of cardiac muscle of a mammal which comprises systemically administering such compounds to a mammal.

9 Claims, No Drawings

N-HYDROXY-5-PHENYL-2-FURANCARBOX-IMIDAMIDES USEFUL AS CARDIOTONIC AGENTS

TECHNICAL FIELD

The present invention relates to compounds and compositions which are useful as cardiotonic agents, and to the treatment of a mammal to increase the contractility of its heart.

BACKGROUND OF THE INVENTION

Heart failure is an abnormality in cardiac function that results from the inability of the heart to pump blood commensurate with the body's needs. Failure develops from a depression in myocardial contractility which can occur due to ischemic heart disease, hypertension, non-obtrusive cardiomyopathies and certain types of congenital heart disease.

As used herein, a cardiotonic agent is a substance which increases the force of contraction of heart muscle of a mammal to which it is administered. It is advantageous to achieve such increased cardiac contractile force with little or no increase in the rate of heartbeat of the mammal.

Certain N-hydroxy-5-phenyl-2-furancarboximidamides are known and have been disclosed to have antidepressant activity. U.S. Pat. No. 3,946,049 issued to Pelosi on Mar. 23, 1976, discloses certain N-hydroxy-5-phenyl-2-furancarboximidamides and methods of synthesizing them and is hereby incorporated by reference.

References which disclose compounds having structures similar to the N-hydroxy-5-phenyl-2-furancarboximidamides of the present invention includes the following U.S. Pat. Nos.: 4,012,414 issued to Pelosi on Mar. 15, 1977; 4,012,415 issued to Pelosi & Yu on Mar. 15, 1977; 4,012,416 issued on Pelosi on Mar. 15, 1977; 4,021,444 issued to Pelosi on May 3, 1977; and 4,022,798 issued to Pelosi on May 10, 1977.

References which disclose certain cardiotonic agents include the following U.S. Pat. Nos.: 3,985,891 issued to Kutter, Austel & Diederen on Oct. 12, 1976; 4,004,012 issued to Lesher & Opalka on Jan. 18, 1977; 4,032,575 issued to Ikezaki, Ito, Okazaki, Hoshiyama, Nagao & Nakajima on June 28, 1977; 4,289,772 issued to Campbell, Danilewicz, Evans & Ham on Sept. 15, 1981; 4,297,360 issued to Lesher, Opalka & Page on Oct. 27, 1981; 4,397,854 issued to Sircar on Aug. 9, 1983; 4,405,635 issued to Schnettler, Dage & Grisar on Sept. 20, 1983; and 4,705,782 issued to Logan, Redpath & Roy on Nov. 10, 1987; and European patent applications of Akzo N. V.: 0,158,380 published Oct. 16, 1985, and 0,199,393 published Oct. 29, 1986.

It is an object of the present invention to provide a method of increasing the contractile force of cardiac muscle of a mammal.

It is also an object of this invention to provide novel compounds which increase the contractile force of cardiac muscle of a mammal.

It is also an object of this invention to provide pharmaceutical compositions which increase the contractile force of cardiac muscle of a mammal.

SUMMARY OF THE INVENTION

The present invention provides a method for increasing the contractile force of cardiac muscle of a mammal which comprises systemically administering to such mammal an effective amount of a composition comprising a compound conforming to the following chemical structure:

<chemical structure: R-phenyl-furan-C(=N-OH)-NR$^1$$_2$> wherein
R is nil or mono-, di-, or tri-substituents comprising 2-halo, 3-halo, 4-halo, 3-trifluoromethyl, 4-trifluoromethyl, 3-methyl, 3-ethyl, 3-methoxy, 3-ethoxy, 3-methoxycarbonyl, 4-methoxycarbonyl, 3-ethoxycarbonyl or 4-ethoxycarbonyl; each
R$^1$ is independently hydrogen or lower alkyl;
and pharmaceutically acceptable salts and/or hydrates thereof. The present invention also provides novel compounds and pharmaceutical compositions.

DETAILED DESCRIPTION OF THE INVENTION

In one of its aspects, the present invention is a method for increasing the contractile force of cardiac muscle of a mammal which comprises systemically administering to a mammal having a depressed level of cardiac output an effective amount of a composition comprising certain N-hydroxy-5-phenyl-2-furancarboximidamides as cardiotonic agents. The N-hydroxy-5-phenyl-2-furancarboximidamides found to be useful as cardiotonic agents conform to the chemical structure:

<chemical structure: R-phenyl-furan-C(=N-OH)-NR$^1$$_2$> wherein
R is nil (hydrogens in positions 2, 3, 4, 5 & 6) or mono-, di-, or tri-substituents comprising 2-halo, 3-halo, 4-halo, 3-trifluoromethyl, 4-trifluoromethyl, 3-methyl, 3-ethyl, 3-methoxy, 3-ethoxy, 3-methoxycarbonyl, 4-methoxycarbonyl, 3-ethoxycarbonyl or 4-ethoxycarbonyl;
each R$^1$ is independently hydrogen or lower alkyl;
and pharmaceutically acceptable salts and/or hydrates thereof (Compounds M). Other substituents R which can be present in addition to the aforenamed substituents include, for example, the aforenamed substituents in other positions, hydroxy, amino, nitro, lower alkyl and other common phenyl substituents; preferred other substituents R include halo, trifluoromethyl, methyl, ethyl, methoxy, ethoxy, methoxycarbonyl, ethoxycarbonyl, hydroxy, amino, and nitro.

Preferred N-hydroxy-5-phenyl-2-furancarboximidamides useful in the present invention include compounds which conform to the chemical structure of Compounds M wherein R is nil or comprises 2-chloro, 3-chloro, 4-chloro, 3-fluoro, 2-bromo, 3-bromo, 4-bromo, 3-trifluoromethyl, 4-trifluoromethyl, 3-methyl, 3-methoxy, 3-ethoxycarbonyl, or 4-ethoxycarbonyl. More preferred compounds are Compounds M wherein R is nil or comprises a 2-, 3- or 4-halo, or 3- or 4-trifluoromethyl, especially 3-trifluoromethyl. Other more preferred compounds are Compounds M wherein R is nil or is selected from the group consisting of 3-fluoro, 2-chloro, 3-chloro, 4-chloro, 2-bromo, 3-bromo, 4- bromo, 3-trifluoromethyl, 4-trifluoromethyl, 3-methyl, 3,4-dichloro, 3-methyl-4-bromo, 3-methoxy-4-bromo, 3-chloro-4-methoxy, 3-trifluoromethyl-4-methoxy, 3,4-dimethoxy, 3-ethoxycarbonyl, 4-ethoxycarbonyl, 3-trifluoromethyl-4-hydroxy, 3-trifluoromethyl-4-amino, 3-trifluoromethyl-4-nitro, and 3-trifluoromethyl-5-hydroxy.

N-hydroxy-5-phenyl-2-furancarboximidamides useful in the present invention include compounds which conform to the chemical structure of Compounds M wherein each $R^1$ is independently hydrogen or lower alkyl. As used herein, $R^1$ being lower alkyl means that $R^1$ is $C_1$ to about $C_6$ straight or branched alkyl or the two $R^1$'s are attached to form a $C_2$ to about $C_6$ ring with the included nitrogen. Preferably each $R^1$ is independently hydrogen, methyl, or ethyl; most preferably each $R^1$ is hydrogen.

The cardiotonic activity of compounds of the present invention can be demonstrated using the primary screening test method set forth in the following reference: Evans, D. B., R. E. Weishaar & H. R. Kaplan, "Strategy for the Discovery and Development of a Positive Inotropic Agent", *Pharmacology and Therapeutics*, Vol. 16 (1982), pp. 303–330. This test measures the effects of such compounds on the contractility of cardiac tissue excised from the papillary muscle of a guinea pig.

Compounds of the present invention have demonstrated increased cardiac contractility according to the above screening test.

TEST METHODS

TEST METHOD I

In Vitro Guinea Pig Papillary Muscle Contractile Force Measurement

Unfasted male Hartley albino guinea pigs, weighing 450–650 g (Charles River Breeding Laboratories, Inc., Wilmington, MA) are used in these studies. The animals are first heparinized (100 U/kg ip), and anesthetized with pentobarbital sodium, 35 mg/kg ip, 5–10 minutes prior to sacrifice. After sacrificing the animal, the heart is quickly removed into a Petri dish filled with a solution of the following composition (in water): NaCl 118.4 mM; dextrose 11.0 mM; KCl 4.7 mM; $MgSO_4$ 1.2 mM; $NaH_2PO_4$ 1.3 mM; $CaCl_2.2H_2O$ 2.5 mM; $NaHCO_3$ 25.01 mM; aerated with 95% $O_2$:5% $CO_2$ at room temperature. The heart is stimulated by an electric field of 30 v, 4 msec, 1 Hz in the dissecting dish.

Papillary muscle segments 5–10 mm in length are dissected from right and left ventricles, and the tissues are mounted from hooks in organ baths maintained at 30° C. The ligatures are tied to Grass FTO3 force-displacement transducers with an initial tension of 1 gram. Responses are measured in grams of developed tension and recorded with a Grass Model 7 polygraph. Electrical stimuli to the papillary muscles are delivered through platinum pin electrodes placed in the bath medium without touching the tissues, i.e. field stimulation, with the following square wave parameters; 10 v; 4 msec; 1 Hz, as soon as they are put into the baths. After a short time, voltage is increased until stable responses are obtained (10–25% above threshold). The tissues are allowed to equilibrate under such stimulation for at least 1 hour before experimentation.

Compounds to be tested for cardiotonic activity are dissolved in a solvent system composed of 90% polyethylene glycol (PEG) 400 (Sigma 93F-0490), 6% ethanol (95%), 3% propylene glycol and 1% distilled water, unless they have sufficient solubility in distilled water. The stock solution is 10 mM to permit injection volumes of 10 and 90 μl, reaching final cumulative bath concentrations of 10 and 100 μM.

Isoproterenol (1, 3 or 10 nM) is given at the beginning of each experiment to confirm the viability and responsiveness of the tissues. Propranolol, 10 μM is then added to the tissue baths containing papillary muscle strips in order to exclude cardiotonic effects dependent on catecholamine-related mechanisms or β-adrenergic activation. Responsiveness to isoproterenol or other known cardiotonic agents is also assessed at the end of the experiment unless positive responses to tested compounds are obtained near the end of testing.

Another aspect of the present invention is certain N-hydroxy-5-phenyl-2-furancarboximidamides which are novel compounds and are useful as cardiotonic agents.

Novel compounds of the present invention include compounds of the class of N-hydroxy-5-phenyl-2-furancarboximidamides which conform to the chemical structure of Compounds M except for such N-hydroxy-5-phenyl-2-furancarboximidamides which are disclosed in U.S. Pat. No. 3,946,049 incorporated by reference hereinabove. Novel compounds of the present invention include Compounds M, except where R is nil or 4-chloro and both $R^1$'s are hydrogen (Compounds N).

Preferred novel compounds of the present invention include Compounds N wherein R comprises 2-chloro, 3-chloro, 3-fluoro, 2bromo, 3-bromo, 4-bromo, 3-trifluoromethyl, 4-trifluoromethyl, 3-methyl, 3-methoxy, 3-ethoxycarbonyl or 4-ethoxycarbonyl. More preferred novel compounds of the present invention include Compounds N wherein R comprises 2-, 3- or 4-halo, or 3- or 4-trifluoromethyl, especially 3-trifluoromethyl. Other more preferred novel compounds include Compounds N wherein R is selected from the group consisting of 3-fluoro, 2-chloro, 3-chloro, 2-bromo, 3-bromo, 4-bromo, 3-trifluoromethyl, 4-trifluoromethyl, 3-methyl, 3,4-dichloro, 3-methyl-4-bromo, 3-methoxy-4-bromo, 3-chloro-4-methoxy, 3-trifluoromethyl-4-methoxy, 3,4-dimethoxy, 3-ethoxycarbonyl, 4-ethoxycarbonyl, 3-trifluoromethyl-4-hydroxy, 3-trifluoromethyl-4-amino, 3-trifluoromethyl-4-nitro, and 3-trifluoromethyl-5-hydroxy.

Furthermore, novel compounds of the present invention include Compounds N wherein each $R^1$ is hydrogen or lower alkyl. Preferred is each $R^1$ being independently hydrogen, methyl or ethyl; most preferred is each $R^1$ being hydrogen.

Compounds of the present invention can be synthesized using the following general stepwise procedure or a modification thereof which is within the purview of a skilled organic chemist:

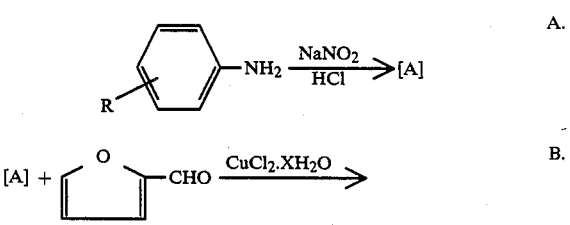

-continued

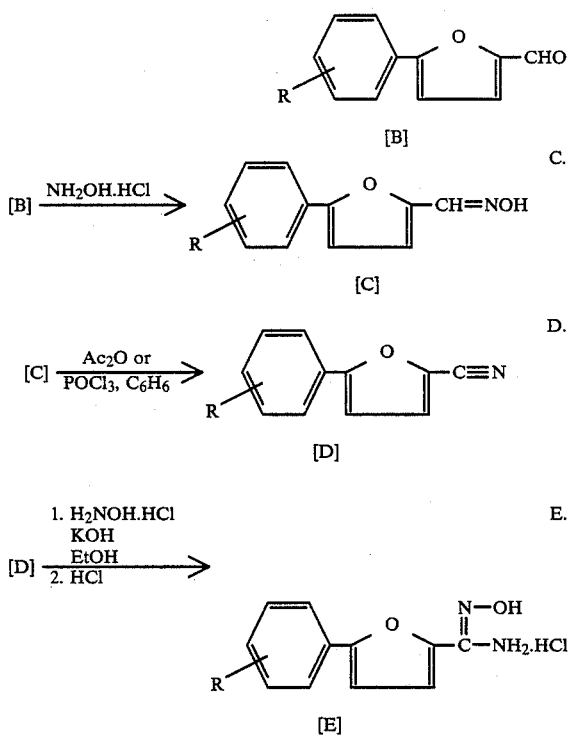

The following non-limiting examples provide methods for synthesizing the novel compounds of the present invention. All temperatures are given in °C.

EXAMPLE 1

5-(4-Bromo-3-methoxyphenyl)-N-hydroxy-2-furancarboximidamide Hydrochloride

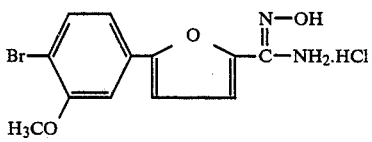

2-Bromo-5-nitroanisole (25 g, 0.116 mole) (Fairfield Chemical Co., Blythewood, S.C.) was dissolved in 150 ml of 70:30 methanol/ethyl acetate. Raney nickel (1.0 g) was added to the solution. The mixture was hydrogenated on a Parr shaker for 3 hours, then filtered through Celite. The dark brown filtrate was treated with Darco and concentrated under reduced pressure to a brown solid. The solid was dissolved in 50:50 ethyl acetate/hexane (1 L) and filtered through a 2-inch cake of silica gel (column grade). The resulting solution was concentrated under reduced pressure to a solid yielding 19.3 g (89% yield) of 4-bromo-3-anisidine (O). The NMR was consistent with the structure of O.

A. & B.

4-Bromo-3-anisidine (17.5 g, 0.093 mole) was stirred in distilled water (150 ml) containing concentrated HCl (30 ml) and cooled to 0° in an ice water bath. A solution of sodium nitrite (6.4 g, 0.093 mole) in water (30 ml) was added and the mixture was stirred at 0°. After 1 hour, furfural (11.17 g, 0.116 mole) and cupric chloride dihydrate (5.11 g, 0.004 mole) were added. The mixture was allowed to warm to room temperature and stir for 72 hours. The reaction was then filtered yielding 22.43 g (86% yield) of a dark brown solid product, 5-(4-bromo-3-methoxyphenyl)-2-furancarboxaldehyde (B). The IR was consistent with the structure of B (aldehyde carbonyl at 1660 cm$^{-1}$).

C. & D.

B (19.6 g, 0.070 mole), anhydrous sodium acetate (11.48 g, 0.14 mole) and hydroxylamie hydrochloride (9.73 g, 0.14 mole) were combined and refluxed in SDA-32 (400 ml) (ethanol:ethyl ether at 100:5 volume:volume-U.S. Industrial Chemical Co., Westport, CN) containing water (31 ml) for 5 hours. Heat was removed and the mixture was allowed to cool to room temperature and stir for 20 hours. The reaction was then poured into ice water and upon warming to room temperature, a solid formed. The solid oxime was collected by filtration and allowed to air dry for 20 hours.

The above oxime was refluxed in acetic anhydride (400 ml) for 2.5 hours. The solution was poured into crushed ice and allowed to stand for 20 hours. The solid that formed was collected by filtration and air dried. The solid was then dissolved in 1.5 L of 1:3 ethyl acetate/hexane and stirred for 0.5 hour with 200 g of silica gel. The mixture was filtered and the filtrate was concentrated under reduced pressure to an orange solid yielding 9.82 g (57% yield) of product, 5-(4-bromo-3-methoxyphenyl)-2-furonitrile (D). The IR was consistent with the structure of D (nitrile at 2245 cm$^{-1}$).

E.

D (2.72 g, 0.01 mole) was dissolved in ethanol (100 ml). Hydroxylamine hydrochloride (Aldrich Chemical Co., Milwaukee, WI) (0.7 g, 0.01 mole) and potassium hydroxide (0.56 g, 0.01 mole) were added and the reaction was refluxed for 5 hours. Upon cooling to room temperature, the reaction was filtered to remove insoluble material and the filtrate was concentrated under reduced pressure to a solid. The insolubles and solid were combined, stirred with water and collected by filtration. The resulting solid was suspended in methanol (10 ml). Methanolic hydrochloric acid was added dropwise until an acidic (pH paper) solution formed. The solution was cooled in an ice bath and ether was added to precipitate a solid. The solid was collected by filtration and dried in vacuo at 77° yielding 2.26 g (b 59% yield) of 5-(4-bromo-3-methoxyphenyl)-N-hydroxy-2-furancarboximidamide hydrochloride (E). The IR, NMR and mass spectrum were consistent with the structure of E.

Anal. calc'd for $C_{12}H_{11}BrN_2O_3 \cdot HCl$: C, 41.47; H, 3.48; N, 8.06, Found: C, 41.17; H, 3.58; N, 7.70.

EXAMPLE 2

5-(3-Fluorophenyl)-N-hydroxy-2-furanecarboximidamide Hydrochloride

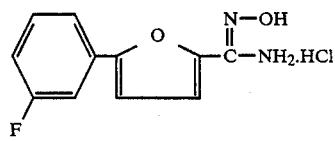

A. & B.

To a stirring mixture of 3-fluoroaniline (Aldrich Chemical Co.) (73.16 g, 0.658 mole) in concentrated HCl (230 ml) and water (330 ml) at 0° was added dropwise a solution of sodium nitrite (46.06 g, 0.667 mole) in water (265 ml). A temperature of 0°–6° was maintained during the addition. After the addition was complete, the reaction was stirred at 0°–5° for 30 minutes. Then 2-furaldehyde (63.18 g, 0.658 mole) and a solution of copper (II) chloride hydrate (15.13 g) in water (100 ml) were added. The reaction was stirred overnight as the ice gradually melted. A gummy solid was present. The solid was collected by filtration and was dark green in color. The solid was dissolved in chloroform, treated with Darco, filtered, and concentrated to a dark green oily residue. Purification was accomplished by preparative silica gel HPLC (solvent system dichloromethane:hexane:ethyl acetate, 50:50:2) yielding 51.62 g (41% yield) of 5-(3-fluorophenyl)-2-furancarboxaldehyde (B).

C.

B (30 g, 0.158 mole), hydroxylamine hydrochloride (21.96 g, 0.316 mole) and sodium acetate trihydrate (43 g, 0.316 mole) were refluxed in SDA-32 (1 liter) and water (90 ml) for 4.5 hours. The reaction was cooled to room temperature then poured into ice water (6 liters). The precipitate was collected and air dried yielding 27.47 g (85% yield) of 5-(3-fluorophenyl)-2-furancarboxaldehyde oxime (C).

D.

C (27.47 g, 0.134 mole) was refluxed in acetic anhydride (500 ml) for 3 hours. After cooling to near room temperature, the reaction was poured into ice water (3 liters) and allowed to stand for 72 hours. The brown solid which formed was collected and washed well with water. After air drying thoroughly, the yield was 21.48 g. Purification by liquid chromatography on silica gel was necessary (90% hexane/ethyl acetate). After purification, the yield was 15.88 g (63% yield) of 5-(3-fluorophenyl)-2-furonitrile (D).

E.

D (7.0 g, 0.037 mole), hydroxylamine hydrochloride (2.85 g, 0.041 mole) and potassium hydroxide (2.30 g, 0.041 mole) were refluxed in absolute ethanol (250 ml) for 1.5 hours. After cooling, a white solid was filtered off and discarded. The filtrate was concentrated to an oil. The oil was dissolved in ethyl acetate (some methanol was added to aid in solubility) and cooled in an ice bath. The solution was acidified (pH=2–3) by the addition of a saturated HCl/methanol solution. The hydrochloride salt precipitated and was stirred for 30 minutes. The solid was collected by filtration. After drying under high vacuum for 2 days at room temperature and then 2 days at 60°, the yield was 7.80 g (82% yield) of 5-(3-fluorophenyl)-N-hydroxy-2-furancarboximidamide hydrochloride (E). The IR, NMR, and mass spec. were all consistent with the structure of E; m.p. 196°–199° (with decomposition). The TLC showed 1 UV positive spot at $R_f=0.3$ (hexane:ethyl acetate, 3:2).

Anal. calc'd for $C_{11}H_9FN_2O_2\cdot HCl$: C, 51.47; H, 3.93; N, 10.91, Found: C, 51.07; H, 3.91; N, 10.63.

EXAMPLE 3

5-(4-Chlorophenyl)-N-hydroxy-2-furancarboximidamide

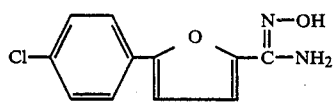

A. & B.

A warm mixture of 4-chloroaniline (Aldrich Chemical Co.) (1000 g, 7.84 moles), water (3142 ml) and concentrated hydrochloric acid (3142 ml) was cooled to 0°. A solution of sodium nitrite (551 g, 8.0 moles) in water (787 ml) was added in 1.5 hours maintaining the reaction at a temperature of 0° to 5°. The reaction solution was stirred an additional 15 minutes. A solution of distilled furfural (787 g, 8.2 moles) in acetonitrile (500 ml) was added followed by a solution of cupric chloride dihydrate (157.2 g, 0.92 mole) in water (787 ml). The cooling bath was removed and the reaction solution was warmed to 20° over 3 hours after which time an orange crystalline solid started precipitating. When the temperature reached 27.5°, a water bath was used to maintain the temperature at 27.5° to 29° for 4 hours. Stirring was continued overnight in the same water bath. The mixture was filtered, and the brown semi-solid was triturated with hexane, filtered, layered with hexane, triturated with SDA-30 (ethanol:methanol at 100:10 volume:volume—U.S. Industrial Chemical Co.), filtered, washed with SDA-30 and dried at 60° to yield 635 g (39% yield) of 5-(4-chlorophenyl)-2-furancarboxaldehyde (B), m.p. 127°–127.5°. An analytical sample was prepared by recrystallization from dimethylformamide and then from acetonitrile, m.p. 130.5°–131.5°.

Anal. calc'd for $C_{11}H_7ClO_2$: C, 63.94; H, 3.41; Cl, 17.16, Found: C, 63.99; H, 3.36; Cl, 17.27.

C. A mixture of 21 g (0.10 mole) of B, 14 g (0.20 mole) of hydroxylamine hydrochloride, 16.5 g (0.20 mole) of anhydrous sodium acetate, 350 ml of 95% ethanol, and 35 ml of water was heated under reflux for 3½ hours. After cooling, the mixture was poured into 1 liter of cold water. The solid which deposited was collected by filtration and dried in 60° oven overnight to give 22 g (100% yield) of 5-(4-chlorophenyl)-2-furancarboxaldehyde oxime (C). One recrystallization from an isopropanol-H$_2$O mixture gave an analytical sample, m.p. 139°–141°.

Anal. calc'd for $C_{11}H_8ClNO_2$: C, 59.61; H, 3.64; N, 6.32 Found: C, 59.60; H, 3.57; N, 6.28

D. A solution of 6.9 g (0.045 mole) of phosphorus oxychloride (Aldrich Chemical Co.) in 10 ml of benzene was added dropwise over 0.5 hour to a stirred, refluxing solution of 20 g (0.09 mole) of C in 350 ml of benzene. The reaction mixture was heated under reflux for 2 hours, cooled and filtered. The filtrate was washed with 5% sodium bicarbonate solution, with water, and dried over MgSO$_4$. Solvent was removed on a rotary evaporator to give 16 g of residual solid. The solid was dissolved in hot MeOH, and water was added to turbidity. The black oily material which was deposited was separated by filtration and discarded. The filtrate was cooled to precipitate a tan solid which was collected by filtration and dried in a 60° oven; weight was 12 g (65% yield) of 5-(4-chlorophenyl)-2-furonitrile (D); m.p. 76°–77°.

Anal. calc'd for $C_{11}H_6ClNO$: C, 64.88; H, 2.97; N, 6.88, Found: C, 64.73; H, 2.99; N, 6.91.

E.

A mixture of 51 g (0.25 mole) of D, 19 g (0.27 mole) of hydroxylamine hydrochloride, 18 g (0.27 mole) of potassium hydroxide and 750 ml of absolute ethanol was heated under reflux for 1 hour. The reaction mixture was concentrated on a rotary evaporator and cooled in ice overnight. The solid was collected by filtration and washed with anhydrous ether to give 43 g (73% yield) of 5-(4-chlorophenyl)-N-hydroxy-2-furancarboximidamide (E). Two recrystallizations from absolute ethanol gave an analytical sample, m.p. 167°–169°.

Anal. calc'd for $C_{11}H_9ClN_2O_2$: C, 55.82; H, 3.83; N, 11.84 Found: C, 55.44; H, 3.78; N, 11.72

EXAMPLE 4

5-(3-Chloro-4-methoxyphenyl)-N-hydroxy-2-furancarboximidamide Hydrochloride

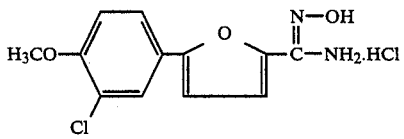

A. & B.

3-Chloro-4-methoxyaniline (Aldrich Chemical Co.) (50.0 g, 0.317 mole), concentrated hydrochloric acid (113 ml) and water (160 ml) were combined and cooled to −5° in an ice/salt/methanol bath. A solution of sodium nitrite (22.57 g, 0.323 mole) in water (130 ml) was added dropwise at a rate such that a temperature of less than 5° was maintained. After the addition was complete, the reaction was stirred at 0°–5° for 30 minutes. Then, all at once, 2-furaldehyde (30.55 g, 0.318 mole) and a solution of copper (II) chloride hydrate (7.31 g) in water (50 ml) were added. The ice bath was allowed to melt gradually overnight. A brown solid was filtered off and washed well with water. The brown solid was air dried yielding 7.79 g. The filtrate was stirred overnight and more solid precipitated. The solid was filtered off, washed with water, washed with 2-propanol and air dried yielding 22.0 g. More solid precipitated out of the filtrate giving a third crop of 15.17 g. The total yield of 5-(3-chloro-4-methoxyphenyl)-2-furancarboxaldehyde (B) was 44.96 g (60% yield). The IR and NMR confirmed the structure of B.

C.

B (17.94 g, 0.076 mole), hydroxylamine hydrochloride (10.57 g, 0.152 mole) and sodium acetate trihydrate (20.68 g, 0.152 mole) were refluxed in SDA-32 (575 ml) and water (50 ml) for 4.5 hours. The reaction was stirred at room temperature for 72 hours. The reaction was poured into ice water (1500 ml) and allowed to stand overnight. A solid was filtered off, air dried overnight, and then dried overnight at 60°. The yield was 17.77 g (93% yield) of 5-(3-chloro-4-methoxyphenyl)-2-furancarboxaldehyde oxime (C). The IR confirmed the structure of C.

D.

C (12.0 g, 0.048 mole) was refluxed in acetic anhydride (180 ml) for 3 hours. After cooling to room temperature, the reaction was poured into ice water (1500 ml) and allowed to stand overnight. The product was extracted into chloroform (600 ml). The organic layer was washed with water (2×250 ml), saturated sodium bicarbonate (2×500 ml) and water (1×500 ml). The solution was dried over magnesium sulfate, treated with Darco, filtered and concentrated to a dark brown solid (9.51 g). Purification by preparative HPLC on silica gel gave 6.30 g (56% yield) of 5-(3-chloro-4-methoxyphenyl)-2-furonitrile (D).

E.

D (5.33 g, 0.0228 mole), hydroxylamine hydrochloride (1.74 g, 0.025 mole) and potassium hydroxide (1.40 g, 0.025 mole) were refluxed in absolute ethanol (125 ml) for 1.5 hours. The reaction was cooled to room temperature. Much solid was present. The solid was collected by filtration and washed numerous times with water, then hexane. After air drying thoroughly the yield was 4.64 g. The solid was dissolved in ethyl acetate. It was necessary to add a small amount of methanol to dissolve the solid completely. The solution was cooled in an ice bath and saturated HCl/methanol was added until the pH reached 3. The hydrochloride salt precipitated and was collected by filtration. The solid was washed with ethyl acetate and air dried to yield 5.03 g of 5-(3-chloro-4-methoxyphenyl)-N-hydroxy-2-furancarboximidamide hydrochloride (E). Recrystallization from methanol (ethyl acetate added to precipitate solid) yielded 3.0 g (43% yield) of E. An analytical sample was dried under high vacuum at 65° and NMR, IR and mass spec. confirmed the structure of E. The TLC was one spot; m.p. 223°–227°.

Anal. calc'd for $C_{12}H_{11}ClN_2O_3 \cdot HCl$: C, 47.55; H, 3.99; N, 9.24, Found: C, 47.35; H, 4.02; N, 9.06.

EXAMPLE 5

5-(4-Methoxy-3-trifluoromethylphenyl)-N-hydroxy-2-furancarboximidamide Hydrochloride

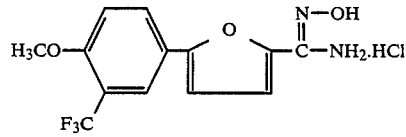

A. & B.

4-Methoxy-3-trifluoromethylaniline (46.54 g, 0.243 mole), concentrated HCl (87 ml) and water (122 ml) were stirred together and cooled to 0°. A solution of sodium nitrite (17.07 g, 0.247 mole) in water (98 ml) was added dropwise, keeping the temperature at 0°–5°. After the addition was complete, the reaction was stirred at 0°–5° for 0.5 hours. Then, all at once, 2-furaldehyde (23.42 g, 0.244 mole) and a solution of copper (II) chloride hydrate (5.60 g) in water (37 ml) were added. The ice bath was allowed to melt gradually as the reaction stirred for 2 days. An oil which had separated was extracted into ethyl acetate (400 ml). The ethyl acetate was washed with water (2×300 ml), dried over MgSO4, treated with Darco and filtered. The solvent was evaporated in vacuo leaving behind a dark oil (55.17 g). The sample required purification by liquid chromatography (solvent: hexane:ethyl acetate 3:1). The yield of purified sample was 16.56 g (25% yield) of 5-(4-methoxy-3-trifluoromethylphenyl)-2-furancarboxaldehyde (B). The IR and NMR confirmed the structure of B.

C.

B (9.01 g, 0.033 mole), hydroxylamine hydrochloride (4.59 g, 0.066 mole) and sodium acetate trihydrate (8.98 g, 0.066 mole) were refluxed in SDA-32 (250 ml) and water (20 ml) for 4.5 hours. The reaction was poured into ice water (600 ml). A light yellow solid separated and was collected by filtration. The solid was air dried yielding 9.24 g (97% yield) of 5-(4-methoxy-3-trifluoromethylphenyl)-2-furancarboxaldehyde oxime (C). The IR confirmed the structure of C.

D.

C (9.24 g, 0.032 mole) was refluxed in acetic anhydride (105 ml) for 3 hours. After cooling, the reaction was poured into ice water (800 ml) and allowed to stand overnight. A brown solid was collected by filtration. The solid was dissolved in chloroform, treated with Darco, filtered and concentrated to a brown solid (6.54 g). The sample required purification by preparative HPLC on silica gel (hexane:chloromethane 7:3). The product-rich fractions yielded a pale yellow solid, 5-(4-methoxy-3-trifluoromethylphenyl)-2-furonitrile (D), (4.48 g, 52% yield) upon evaporation. The NMR and IR confirmed the structure of D.

E.

D (4.38 g, 0.016 mole), hydroxylamine hydrochloride (1.22 g, 0.0176 mole) and potassium hydroxide (0.99 g, 0.0176 mole) were refluxed in absolute ethyl alcohol (60 ml) for 1.5 hours. The reaction was cooled to room temperature and stirred overnight. A white solid was filtered off and discarded. The filtrate was concentrated to a sticky solid. The solid was dissolved in ethyl acetate (it was necessary to add a small amount of methyl alcohol to fully dissolve the solid) and cooled in an ice bath. A saturated solution of HCl/methanol was added. The precipitate was collected by filtration, washed with ethyl acetate, washed with ether and air dried yielding 3.90 g (72% yield) of 5-(4-methoxy-3-trifluoromethylphenyl)-N-hydroxy-2-furancarboximidamide hydrochloride (E). The sample was recrystallized from a mixture of ethyl acetate and methanol yielding 3.31 g (61% yield). An analytical sample was prepared by triturating with water then air drying and finally drying under high vacuum. The NMR, IR, and mass spec. were all consistent with the structure of E; m.p. 203°–211°. The TLC showed one spot.

Anal. calc'd for $C_{13}H_{11}F_3N_2O_3 \cdot HCl$: C, 46.37; H, 3.59; N, 8.32, Found: C, 46.62; H, 3.57; N, 8.17.

EXAMPLE 6

5-(4-Bromo-3-methylphenyl)-N-hydroxy-2-furancarboximidamide Hydrochloride

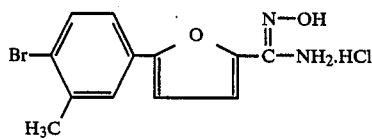

A. & B.

18.6 g (0.1 mole) of 4-bromo-3-methylaniline (Fairfield Chem.) was stirred with 250 ml of 6N HCl. The suspension was stirred in a MeOH, ice, NaCl bath until the temperature of the reaction mixture was less than 0°. 7.2 g (0.105 mole) of sodium nitrite in 50 ml of water was added, at a rate at which the reaction temperature did not raise above 0°. The solution was stirred cold for 1 hour following addition. At that time, 10.6 ml (0.13 mole) of furaldehyde (freshly distilled) was added followed by 2.3 g (0.017 mole) of copper (II) chloride in water. The bright green solution was stirred at room temperature overnight; a green solution still remained, which contained a black oily residue. The oily residue was extracted out with 500 ml of chloroform. The chloroform was treated with Darco and MgSO4 to yield a black oil, 24.2 g. The black oil was then triturated with ethyl ether to yield 2 crops of a light brown solid weighing 5.9 g (22% yield) of 4-bromo-3-methylphenyl-furaldehyde (B). IR and TLC confirmed the structure of B.

C. & D.

5.9 g (0.022 mole) of B was mixed with 200 ml of 95% ethanol and 20 ml of water. To the mixture was added 3.06 g (0.044 mole) of hydroxylamine .HCl and 3.61 g (0.044 mole) of sodium acetate. The solution was refluxed overnight. The reaction solution was cooled to room temperature and the ethanol was evaporated off. The residue was triturated with 250 ml of water. A tan solid (oxime) was filtered and then oven dried at 60° for 3 hours. This solid was refluxed with 200 ml of acetic anhydride overnight. The resulting black solution was cooled to room temperature and then poured into 1000 ml of ice water. The oily-ice mixture was stirred for 5 hours before a solid formed which was then filtered and washed with additional water. The solid was air dried to yield 5.3 g (92% yield) of 4-bromo-3-methylphenyl-furonitrile (D).

E. 2.62 g (0.01 mole) of D was dissolved in 75 ml of abs. EtOH. To that solution was added 0.76 g (0.011 mole) of hydroxylamine .HCl and 0.62 g (0.011 mole) of crushed potassium hydroxide. The suspension was refluxed for 2 hours and then it sat at room temperature for 3 days. The reaction suspension was poured into 500 ml of ice water. A light-colored solid was filtered off and air dried to yield 2.77 g (94% yield) of 5-(4-bromo-3-methylphenyl)-N-hydroxy-2-furancarboximidamide (E1). A 1 gram portion was converted to the hydrochloride salt using MeOH, MeOH/HCl, and ethyl ether. The solid was then dried at 100° in an oven overnight to yield 0.9 g of 5-(4-bromo-3-methylphenyl)-N-hydroxy-2-furancarboximidamide .HCl (E2). The MS, IR, and NMR were consistent with structure of E2, and the m.p. was 239° with decomposition.

Anal. calc'd for $C_{12}H_{11}BrN_2O_2 \cdot HCl$: C, 43.46; H, 3.65; N, 8.45, Found: C, 43.62; H, 3.54; N, 8.22.

EXAMPLE 7

5-(4-Hydroxy-3-trifluoromethylphenyl)-N-hydroxy-2-furancarboximidamide Hydrochloride

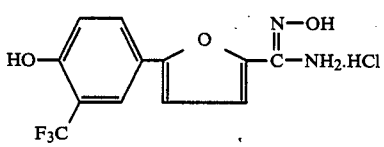

To a 100 ml round bottom flask equipped with stir bar and condenser and heated in an oil bath was added 4.04 g (0.014 mole) of 5-(4-methoxy-3-trifluoromethylphenyl)-2-furonitrile (Compound D from EXAMPLE 5 hereinabove), 3.66 ml (3.19 g, 0.021 mole, 1.5 equiv.) of phenyltrimethylsilane (Aldrich Chemical Co.), 5.33 g (0.021 mole, 1.5 equiv.) of iodine and 25 ml of dry toluene. This stirring slurry was heated to reflux for 48 hours. The TLC showed that the reaction was mostly complete, so it was cooled to room temperature and diluted with 100 ml of toluene; then washed with 3×100 ml of 10% NaHSO3 solution and 2×100 ml of distilled water. It was dried over MgSO4, then filtered and the filtrate was evaporated under vacuum to yield 7.0 g of brown solid. This crude product was chromatographed on silica gel using 50% EtOAc/hexane. The purified fractions were evaporated to yield a tan solid. This was further purified by silica gel chromatography using 15% EtOAc/hexane. Appropriate fractions were combined and evaporated to yield 2.3 g of a tan solid. This was still impure, so it was run through two silica gel columns using first 15% EtOAc/hexane, then second, 1% methanol/dichloromethane. Finally the fractions were TLC'd, combined and evaporated to yield a white solid, 1.69 g of 5-(4-hydroxy-3-trifluoromethylphenyl)-2-furonitrile (F). $R_f$=0.28 (CH2Cl2).

E.

In a 125 ml, 3-necked round bottom flask equipped with thermometer, condenser, stir bar and heated in an oil bath was added 1.69 g (0.0067 mole) of F, 0.507 g (0.0073 mole, 1.1 equiv.) of hydroxylamine hydrochloride, 0.409 g (0.0073 mole, 1.1 equiv.) of potassium hydroxide and 40 ml of abs. ethanol. This yellow slurry was stirred and heated to reflux for 3 hours, then stirred at room temperature overnight. TLC showed the reaction to be complete, so the slurry was filtered and rinsed with 50 ml of ethanol. The ethanol was evaporated off under vacuum to yield a tan solid. This solid was dissolved in 200 ml of ethyl acetate and washed with 2×100 ml of distilled water, dried over $MgSO_4$, filtered and evaporated to yield 1.92 g of crude product. This crude product was eluted through a silica gel column using 60% EtOAc/hexane. After collecting the fractions and TLCing them, the clean fractions were combined and evaporated to yield 1.7 g of 5-(4-hydroxy-3-trifluoromethylphenyl)-N-hydroxy-2-furancarboximidamide (E1). E1 was dissolved in 50 ml of ether in a 100 ml flask and then acidified with methanolic/HCl to a pH of 1–3. After stirring for a few minutes, a pink solid precipitated. This was filtered and air dried to yield 1.68 g. TLC showed two spots, so the crude product was dissolved in 10 ml of methanol, then the pH was adjusted to basic side with 10% $NaHCO_3$ solution to remove the HCl salt. A white solid precipitated and was filtered and air dried to yield 1.49 g. TLC—$R_f$=0.45 (10% $MeOH/CHCl_3$) gave one spot. This pure product was dissolved in 50 ml of ether and acidified with methanolic/HCl solution to a pH of 1–3 and a white solid precipitated. This white solid was filtered and air dried to yield 1.4 g of 5-(4-hydroxy-3-trifluoromethylphenyl)-N-hydroxy-2-furancarboximidamide hydrochloride (E2). TLC—$R_f$=0.27 (10% $MeOH/CHCl_3$). IR and NMR were consistent with a structure of E2.

Anal. calc'd for $C_{12}H_9F_3N_2O_3 \cdot HCl$: C, 44.67; H, 3.12; N, 8.68 Found: C, 44.82; H, 3.24; N, 8.44.

EXAMPLE 8

5-(4-Nitro-3-trifluoromethylphenyl)-N-hydroxy-2-furancarboximidamide Hydrochloride

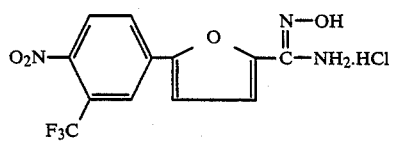

A. & B.

15.23 g (0.074 mole) of 5-amino-2-nitrobenzotrifluoride (Alfa Products) was stirred with 300 ml of 6N HCl. The thick brown suspension was stirred at 0° to −10° during the slow addition of 5.38 g (0.078 mole) of sodium nitrate in 15 ml of water. A solution formed which was stirred cold for 1 hour, following the addition, 7.1 ml (0.074 mole) of furaldehyde (freshly distilled) was poured in followed by 2.1 g (0.0123 mole) of cupric chloride .$2H_2O$ in 10 ml of water. The ice bath was allowed to melt so that the reaction warmed to room temperature slowly. The reaction was stirred at room temperature for 5 days. A dark green oil formed which was extracted out with 3×200 ml of ethyl ether. The ether was treated with $MgSO_4$, Darco and evaporated to yield 18.5 g of a dark green oil. The oil had several spots by TLC so it was purified by silica gel chromatography using 40:60 EtOAc:hexane. The yield was 1.92 g of 5-(4-nitro-3-trifluoromethylphenylfuraldehyde (B). TLC confirmed the structure of B.

C. & D.

2.81 g (0.01 mole) of B was mixed with 1.4 g (0.02 mole) of hydroxylamine .HCl, 1.6 g (0.02 mole) of sodium acetate and 100 ml of 95% EtOH. 10 ml of water was added which brought everything into solution. The solution was refluxed overnight. The reaction was placed on an evaporator until most of the EtOH was gone; it was then poured into ice water. A bright yellow solid precipitated out which was filtered off and air dried to yield 2.65 g of solid. This solid was refluxed with 100 ml of acetic anhydride overnight. The clear dark solution was poured into 1000 ml of ice water and stirred overnight. By morning a dark brown suspension remained. The brown solid was filtered, washed with water and air dried several hours to yield 2.3 g (82% yield) of 5-(4-nitro-3-trifluoromethylphenyl)-2-furonitrile (D).

E.

2.3 g (0.008 mole) of D was stirred with 75 ml of abs. EtOH, 0.61 g (0.0088 mole) of hydroxylamine hydrochloride and 0.49 g (0.0088 mole) of crushed potassium hydroxide. The brown suspension was refluxed for 2 hours and then sat at room temperature overnight. The suspension was poured into 500 ml of water and an orange solid instantly precipitated out. The suspension continued to stir several minutes and then was filtered and the solid was air dried for 5 hours. The yield was 2.3 g (91% yield) of 5-(4-nitro-3-trifluoromethylphenyl)-N-hydroxy-2-furancarboximidamide (E1). 1 g of E1 was converted to its HCl salt (E2) using MeOH, MeOH/HCl, ethyl ether. The product was a tan solid which was dried at 100° in vacuum overnight. The IR, NMR and MS were consistent with structure of E2, and the m.p. was 221° with decomposition.

Anal. calc'd for $C_{12}H_8F_3N_3O_4 \cdot HCl$: C, 40.99; H, 2.58; N, 11.95; Found: C, 41.13; H, 2.59; N, 11.78.

EXAMPLE 9

5-(3-Trifluoromethylphenyl)-N-hydroxy-2-furancarboximidamide Hydrochloride

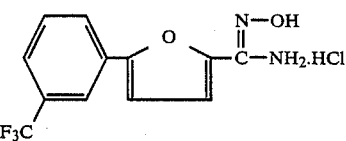

A. & B.

A mixture of 3-aminobenzotrifluoride (180.97 g; 1.12 mole) in 150 ml of $H_2O$ and 300 ml of conc. HCl was stirred in an ice bath. To this was added dropwise a solution of 77.85 g (1.13 mole) of sodium nitrite in 300 ml of $H_2O$ at such a rate as to maintain the reaction temperature below 5°. Following the addition the reaction was stirred for 1 hour, at which time 2-furaldehyde (138.9 g; 1.45 mole) was added followed by a solution of copper (II) chloride dihydrate (22.7 g) in 70 ml of $H_2O$. The reaction was stirred overnight during which time it was allowed to warm to room temperature. It was then extracted with 3×500 ml of ether. The combined extracts were treated with Darco, dried with $MgSO_4$, and filtered. The ether was removed from the filtrate, affording a black oil. This was extracted with 450 ml of hot hexane. The residual, insoluble oil was purified by preparative HPLC on silica gel using CH$_2$Cl$_2$:hexane:ethyl acetate (30:68:2) as eluant. The appropriate fractions were combined and evaporated to dryness under vacuum. The residue was triturated with isopropanol and filtered to yield 62.4 g (23% yield) of 5-(3-trifluoromethylphenyl)-2-(furaldehyde (B) as a pale yellow solid; m.p. 184°–190°.

C. & D.

A mixture of B (60 g, 0.25 mole), hydroxylamine hydrochloride (30 g, 0.50 mole) and anhydrous sodium acetate (41 g, 0.50 mole) in 750 ml SDA-30 and 75 ml water was heated under reflux for 3½ hours. After cooling, the mixture was poured into 1250 ml of cold water. The solid that deposited was collected by filtration and air dried to give 54 g (84% yield) of the oxime, m.p. 70°–72°. A stirred solution of 54 g (0.21 mole) of this solid oxime and 550 ml of acetic anhydride was refluxed for 2½ hours. The solution was cooled, stirred overnight, and poured into 3 liters of ice water. The brown oil solidified after stiring overnight and yielded 51 g (100% yield) of 5-(3-trifluoromethylphenyl)-2-furonitrile (D). A small sample was recrystallized twice from cyclohexane; m.p. 61°–64°.

E.

A one-liter 3-necked flask equipped with stirrer, thermometer and reflux condenser with "Drierite" tube was charged with D (28.4 g, 0.12 mole), hydroxylamine hydrochloride (8.7 g, 0.125 mole), KOH (7.5 g, 0.134 mole) and absolute ethanol (400 ml). The reaction was heated to reflux (79°) for 1.5 hours. The mixture was ice cooled and the insolubles (9.9 g) filtered off. The filtrate was evaporated to dryness on a rotary evaporator. The residue, a viscous oil, was triturated with water and decanted three times. A semi-solid was obtained which was dissolved in anhydrous ether (ca. 1 liter). Gaseous HCl was introduced, and the resulting mixture was filtered and washed with anhydrous ether and dried at 60°. 29 g of 5-(3-trifluoromethylphenyl)-N-hydroxy-2-furancarboximidamide hydrochloride (E) was obtained. Yield: 79%. m.p. 205°–206°. An analytical sample was prepared by dissolving E in SDA-32 and precipitating it with anhydrous ether. This material was recrystallized from acetonitrile; m.p. 202°–204°.

Anal. calc'd for C$_{12}$H$_9$F$_3$N$_2$O$_2$.HCl: C, 47.00; H, 3.29; N, 9.14 Found: C, 46.99; H, 3.22; N, 9.15

EXAMPLE 10

5-(3-Methylphenyl)-N-hydroxy-2-furancarboximidamide Hydrochloride

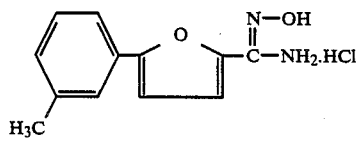

0.5 g (0.0017 mole) of 5-(4-bromo-3-methylphenyl)-N-hydroxy-2-furancarboximidamide (Compound E1 from EXAMPLE 6 hereinabove) was dissolved in 125 ml of abs. MeOH which contained 0.139 g (0.0017 mole) of anhydrous sodium acetate. To this solution 0.2 g of 5% palladium-on-carbon 50% w/w was added. The suspension was hydrogenated on a Parr shaker. The total uptake of hydrogen was 2 lbs. within the first hour. It was then shaken an additional hour without further uptake. The suspension was removed from the shaker and filtered through Celite. The methanol was evaporated to dryness to yield a gummy solid which was triturated with ethyl acetate and the insolubles were discarded. The ethyl acetate filtrate was washed with saturated sodium bicarbonate followed by water. The ethyl acetate was then treated with MgSO$_4$ and evaporated to dryness to yield 0.2 g of a golden oil. The oil was converted to the HCl salt using MeOH, MeOH/HCl, ethyl ether to yield 0.13 g of 5-(3-methylphenyl)-N-hydroxy-2-furancarboximidamide hydrochloride which was dried under vacuum overnight. The IR, NMR, and MS were consistent with this structure, and the m.p. was 184°–188° corrected.

Anal. calc'd for C$_{12}$H$_{12}$N$_2$O$_2$.HCl: C, 57.04; H, 5.19; N, 11.09 Found: C, 56.79; H, 5.25; N, 10.90

EXAMPLE 11

5-(4-Amino-3-trifluoromethylphenyl)-N-hydroxy-2-furancarboximidamide Dihydrochloride

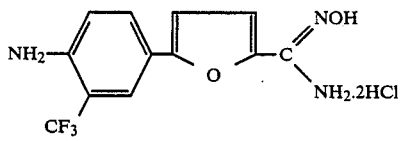

1.4 g (0.0044 mole) of 5-(4-nitro-3-trifluoromethylphenyl)-N-hydroxy-2furancarboximidamide (compound E1 from EXAMPLE 8 hereinabove) was dissolved in 125 ml of abs. methanol. To this solution was added 0.2 g of 5% palladium on activated carbon (50% wet). This black suspension was placed on a Parr shaker and was hydrogenated at 40 psi for 1.5 hours. The reaction suspension was then filtered through Celite and the filtrate was evaporated to dryness to yield 1.4 g of a brown solid. This impure solid was then stirred with 50 ml of absolute ethanol and filtered. The insoluble solid was discarded. The ethanol filtrate was evaporated to dryness. The residue was twice chromatographed on silica gel, the first time using 2.5% methanol in chloroform as eluant, the second time using 60% ethyl acetate in hexane. The isolated material was dissolved in methanol HCl and was precipitated as the HCl salt with ether. This precipitate was dissolved in water. The solution was washed with chloroform, treated with Darco, and filtered through Celite. The filtrate was made basic with NaHCO$_3$, and the free base was extracted into CH$_2$Cl$_2$. The solvent was removed and the product was converted to the dihydrochloride salt as above. The yield of 5-(4-amino-3-trifluoromethylphenyl)-N-hydroxy-2-furancarboximidamide dihydrochloride was 0.14 g (9%); m.p. 189°–192°. Thermal gravimetric analysis showed that the product absorbs water on exposure to air.

Anal. calc'd for C$_{12}$H$_{10}$F$_3$N$_3$O$_2$.HCl: C, 40.24; H, 3.38; N, 11.73 Found: C, 39.57; H, 3.47; N, 11.20

EXAMPLE 12

5-(3-Trifluoromethyl-5-hydroxyphenyl)-N-hydroxy-2-furancarboximidamide Hydrochloride

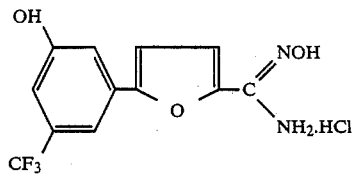

A. & B.

20 g (0.1 mole) of 3-trifluoromethyl-5-methoxyaniline was stirred with 250 ml of 6N HCl. The white suspension was cooled in a methanol/ice/NaCl bath to a temperature of 0°. To this cooled suspension, 7.59 g (0.11 mole) of sodium nitrate in 50 ml of water was slowly added keeping the temperature <0°. A clear solution remained which was stirred at <0° for 1.5 hours. 9.1 ml (0.11 mole) of furaldehyde was added followed by 2.55 g (0.015 mole) of copper (II) chloride .XH$_2$O in 10 ml H$_2$O. This orange solution was allowed to slowly warm to room temperature and stir for 4 days. The orange solution still remained along with a black oily residue. The product was extracted out with 250 ml of CHCl$_3$. The CHCl$_3$ fraction was washed with 2×100 ml of sat. NaHCO$_3$ and 200 ml of water, followed by treatment with Darco and MgSO$_4$. The CHCl$_3$ fraction was then evaporated to dryness to yield 23 g of a dark oil. Purification was obtained by preparative HPLC on silica gel using CH$_2$Cl$_2$ as eluant. The yield of pure 5-(3-trifluoromethyl-5-methoxyphenyl)-2-furancarboxaldehyde (B') was 7 g (26%).

C. & D.

7 g (0.0259 mole) of B' was stirred with 3.6 g (0.0518 mole) of hydroxylamine hydrochloride, 4.2 g (0.0518 mole) of sodium acetate, 150 ml of 95% ethanol and 20 ml of H$_2$O. The clear solution was refluxed overnight.

Most of the 95% ethanol was evaporated off and the remaining suspension was poured into 500 ml of ice water. The suspension was stirred for a few hours and the solid was collected by filtration to yield 6.23 g of solid oxime. 6.23 g of the oxime was dissolved in and refluxed with 200 ml of acetic anhydride overnight. The black solution was then cooled to room temperature and poured into 600 ml of ice water. Several hours of stirring produced a brown solid which was collected by filtration to yield 5.5 g (80%) of 5-(3-trifluoromethyl-5-methoxyphenyl)-2-furonitrile (D').

In a flame dried flask under nitrogen, 4.3 g of D' was dissolved in 200 ml of dry CH$_2$Cl$_2$. The black solution was cooled to −80° in an acetone dry ice bath. To this cold solution, 4.54 ml (0.048 mole) of Boron tribromide was added and the solution was allowed to slowly warm to room temperature and stir overnight. The solution was poured into 1200 ml of ice water and stirred. The product was extracted out with CHCl$_3$, which was then treated with Darco and MgSO$_4$. The CHCl$_3$ fraction was evaporated to dryness to yield 2.5 g golden yellow colored solid. Several hot triturations with EtOAc got rid of highly colored insoluble impurities. The EtOAc solution was evaporated to dryness under vacuum to yield 1.69 g (42%) of 5-(3-trifluoromethyl-5-hydroxyphenyl)-2-furonitrile (D).

E.

1.69 g (0.0067 mole) of D was stirred with 70 ml of absolute EtOH. To this suspension was added 0.42 g (0.0074 mole) of hydroxylamine hydrochloride, followed by 0.51 g (0.0074 mole) of crushed potassium hydroxide. The suspension was refluxed for 2 hours and then sat at room temperature overnight.

The insoluble solid was filtered off and discarded. The filtrate was evaporated to dryness to yield 2.01 g of a golden oily solid, which was then triturated with water and filtered. The solid product was purified by silica gel chromatography using 10% methanol in chloroform as eluant. The purified product was then converted to the HCl salt by dissolving in methanol, making the solution acidic with MeOH/HCl, and precipitating it out with ethyl ether. The yield was 0.4 g (18.5%) of 5-(3-trifluoromethyl-5-hydroxyphenyl)-N-hydroxy-2-furancarboximidamide hydrochloride (E). NMR, IR and MS were consistent with E; m.p.=195°–196°. E was very hydroscopic, a thermal gravimetric analysis (TGA) was run on the same day as the CHN values were run, after the compound had been dried 1 day in vacuum at 100° C. The resulting TGA value showed a total weight loss of 3.33% which was equivalent to 0.618 mole of water.

Anal. calc'd for C$_{12}$H$_9$N$_2$F$_3$O$_3$.HCl.0.618H$_2$O: C, 43.18; H, 3.39; N, 8.39, Found: C, 42.31; H, 3.68; N, 7.45.

Another aspect of the present invention is a composition in dosage unit form comprising an effective amount of the novel N-hydroxy-5-phenyl-2-furancarboximidamides disclosed hereinabove. The composition is preferably adapted to systemic administration to mammals.

As used herein, the term "pharmaceutical carrier" denotes a solid or liquid filler, diluent, or encapsulating substance. Some examples of the substances which can serve as pharmaceutical carriers are sugars, such as lactose, glucose, and sucrose; starches, such as corn starch and potato starch; cellulose and its derivatives, such as sodium carboxymethylcellulose, ethylcellulose, and cellulose acetate; powdered tragacanth; malt; gelatin; talc; stearic acid; magnesium stearate; calcium sulfate; vegetable oils, such as peanut oil, cottonseed oil, sesame oil, olive oil, corn oil, and oil of theobroma; polyols, such as propylene glycol, glycerin, sorbitol, mannitol, and polyethyleneglycol; agar; alignic acid; pyrogen-free water; isotonic salines; and phosphate buffer solutions; as well as other nontoxic compatible substances used in pharmaceutical formulations. Wetting agents and lubricants, such as sodium lauryl sulphate, as well as coloring agents, flavoring agents and preservatives, can also be present.

The pharmaceutical carrier employed in conjunction with the cardiotonic N-hydroxy-5-phenyl-2-furancarboximidamides is used at a concentration sufficient to provide a practical size-to-dosage relationship. Preferably, the pharmaceutical carrier comprises from about 0.1% to about 99% by weight of the total composition.

Preferred dosage unit forms of the compositions of the present invention include capsules, tablets, solutions, and suspensions to be administered orally and solutions and suspensions to be administered parenterally. Preferred dosage unit forms include solutions and suspensions to be administered parenterally comprising from about 10 mg to about 500 mg of a novel cardiotonic N-hydroxy-5-phenyl-2-furancarboximidamides and a suitable pharmaceutical carrier; more preferred is such a unit unit dosage form comprising from about 50 mg to about 200 mg of such compound. Other preferred dosage unit forms include capsules and tablets each comprising from about 50 mg to about 2000 mg of a novel cardiotonic N-hydroxy-5-phenyl-2-furancarboximidamides and a suitable pharmaceutical carrier; more preferred is such a dosage unit form comprising from about 100 mg to about 500 mg of such compound.

While particular embodiments of the present invention have been described, it will be obvious to those skilled in the art that various changes and modifications to the compounds and compositions disclosed herein can be made without departing from the spirit and scope of the invention. It is intended to cover, in the appended claims, all such modifications that are within the scope of this invention.

What is claimed is:

1. A method for increasing the contractile force of cardiac muscle of a mammal which comprises systemically administering to said mammal an effective amount of a composition comprising a compound conforming to the following chemical structure:

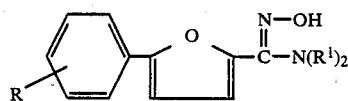

wherein

R is nil or mono-, di- or tri-substituents comprising 2-halo, 3-halo, 4-halo, 3-trifluoromethyl, 4-trifluoromethyl, 3-methyl, 3-ethyl, 3-methoxy, 3-ethoxy, 3-methoxycarbonyl, 4-methoxycarbonyl, 3-ethoxycarbonyl or 4-ethoxycarbonyl; each $R^1$ is independently selected from hydrogen or lower alkyl; or pharmaceutically acceptable salts and hydrates thereof.

2. The method of claim 1 wherein one $R^1$ is hydrogen and the other $R^1$ is selected from hydrogen, methyl or ethyl.

3. The method of claim 1 wherein both $R^1$'s are hydrogen.

4. The method of claim 3 wherein R comprises, as additional substituents, nil, halo, trifluoromethyl, methyl, ethyl, methoxy, ethoxy, methoxycarbonyl, ethoxycarbonyl, hydroxy, amino or nitro.

5. The method of claim 4 wherein R is nil or comprises 2-chloro, 3-chloro, 4-chloro, 3-fluoro, 2-bromo, 3-bromo, 4-bromo, 3-trifluoromethyl, 4-trifluoromethyl, 3-methyl, 3-methoxy, 3-ethoxycarbonyl or 4-ethoxycarbonyl.

6. The method of claim 5 wherein R is nil or mono- or di-substituents.

7. The method of claim 6 wherein R comprises 2-, 3- or 4-halo, or 3- or 4-trifluoromethyl.

8. The method of claim 6 wherein R comprises 3-trifluoromethyl.

9. The method of claim 3 wherein R is nil or is selected from the group consisting of 2-chloro, 3-chloro, 4-chloro, 2-bromo, 3-bromo, 4-bromo, 3-trifluoromethyl, 4-trifluoromethyl, 3-methyl, 3,4-dichloro, 3-methyl-4-bromo, 3-methoxy-4-bromo, 3-chloro-4-methoxy, 3-trifluoromethyl-4-methoxy, 3,4-dimethoxy, 3-ethoxycarbonyl, 4-ethoxycarbonyl, 3-trifluoromethyl-4-hydroxy, 3-trifluoromethyl-4-amino, 3-trifluoromethyl-4-nitro, and 3-trifluoromethyl-5-hydroxy.

* * * * *